(12) United States Patent
Lin et al.

(10) Patent No.: US 11,197,645 B1
(45) Date of Patent: Dec. 14, 2021

(54) SYSTEM AND METHOD OF THROAT ABNORMAL OBJECT RECOGNITION

(71) Applicants: Kaohsiung Chang Gung Memorial Hospital, Kaohsiung (TW); Next E-commerce Technology Co., LTD., Taichung (TW)

(72) Inventors: Wei-Che Lin, Kaohsiung (TW); Yueh-Sheng Chen, Kaohsiung (TW); Sheng-Dean Luo, Kaohsiung (TW); Jian-Feng Lin, Tainan (TW); You-Nan Chen, Taipei (TW)

(73) Assignees: Kaohsiung Chang Gung Memorial Hospital, Kaohsiung (TW); Next E-commerce Technology Co., LTD.

( * ) Notice: Subject to any disclaimer, the term of this patent is extended or adjusted under 35 U.S.C. 154(b) by 0 days.

(21) Appl. No.: 17/079,259

(22) Filed: Oct. 23, 2020

(30) Foreign Application Priority Data

Sep. 4, 2020 (TW) .................................. 109130489

(51) Int. Cl.
| | |
|---|---|
| *A61B 5/00* | (2006.01) |
| *G06K 9/32* | (2006.01) |
| *A61B 6/12* | (2006.01) |
| *A61B 6/00* | (2006.01) |
| *A61B 6/08* | (2006.01) |
| *A61B 90/00* | (2016.01) |

(52) U.S. Cl.
CPC .................. *A61B 6/12* (2013.01); *A61B 6/08* (2013.01); *A61B 6/461* (2013.01); *A61B 6/54* (2013.01); *A61B 90/39* (2016.02); *A61B 2090/3966* (2016.02)

(58) Field of Classification Search
CPC ..... A61B 6/032; A61B 6/5217; A61B 6/5211; A61B 6/03; G06T 7/0012; G06T 7/00; G06T 7/30; G06T 2207/30004; G06T 2207/30196; G06N 20/00; G06N 3/00; G06N 5/00
See application file for complete search history.

(56) References Cited

U.S. PATENT DOCUMENTS 5,807,256 A * 9/1998 Taguchi ................. G16H 50/20
600/425

FOREIGN PATENT DOCUMENTS

CN 111680687 A * 9/2020

\* cited by examiner

*Primary Examiner* — Don K Wong
(74) *Attorney, Agent, or Firm* — Lin & Associates Intellectual Property, Inc.

(57) ABSTRACT

A system and method of throat abnormal object recognition is disclosed. The system includes a throat abnormal object recognition device, a data source device, a display device, and an operation device connected to the throat abnormal object recognition device, the data source device, and the display device. The method includes the throat abnormal object recognition device generating operation parameters, the data source device generating an original X-ray image data, the throat abnormal object recognition device reading the original X-ray image data, performing a pre-stage process on the original X-ray image data to generate a pre-stage processed image data, performing a comparison process on the pre-stage processed image data to generate a comparison processed image data with an abnormal object image, employing a frame mark to mark the abnormal object image as a mark X-ray image, and employing the display device to display the mark X-ray image.

10 Claims, 3 Drawing Sheets

US 11,197,645 B1

SYSTEM AND METHOD OF THROAT ABNORMAL OBJECT RECOGNITION

CROSS-REFERENCE TO RELATED APPLICATION

This application claims the priority of Taiwanese patent application No. 109130489, filed on Sep. 4, 2020, which is incorporated herewith by reference.

BACKGROUND OF THE INVENTION

1. Field of the Invention

The present invention generally relates to a system and method of abnormal object recognition, and more specifically to a system of throat abnormal object recognition provided with a throat abnormal object recognition device, a data source device, a display device, and an operation device connected to the throat abnormal object recognition device, the data source device, and the display device, and a method of throat abnormal object recognition comprising the throat abnormal object recognition device generating operation parameters, the data source device generating an original X-ray image data; the throat abnormal object recognition device reading the original X-ray image data from the operation device, performing a pre-stage process on the original X-ray image data to generate a pre-stage processed image data, performing a comparison process on the pre-stage processed image data to generate a comparison processed image data with an abnormal object image, employing a frame mark to mark the abnormal object image as a mark X-ray image, and employing the display device to display the mark X-ray image.

2. The Prior Arts

As well known, X-ray is a high energy electromagnetic wave with wavelength from about 0.01 to 10 nm (that is, frequency from 30 PHz to 30 EHz). With high penetration, X-ray easily penetrates most materials, and has been widely utilized in various applications to clearly and directly examine internal state or tissues without changing appearance or looks, such as product examination for manufacturing industry, and medical inspection of human body.

Take medical inspection as an example, X-ray is employed to illuminate human body, and the residual X-ray without absorption by human body generates or exposes a responsive X-ray image on an X-ray film. The exposed image is developed by a developing agent to acquire a developed image with gray level. In general, the tissue with lower density absorbs less X-ray, and the responsive image is closer to black such as air in lungs or digestive tract. For the tissue with high density, the absorption of X-ray is high, and the X-ray image is closer to white like bone, metal wearing piece or implant. Thus, the doctor can fast diagnose and clearly understand whether human bones or organs are abnormal according to the X-ray image.

For the patient with bone fracture, the doctor can confirm the bone status through inspecting the X-ray image, and take the best measures for medication.

In addition, the X-ray image is often used to diagnose the abnormal object stuck in the throat part like fish bone. The side view of the neck is usually illuminated by X-ray for inspection of any abnormal object. Since fish bone is similar to ordinary bone in terms of chemical component, a brighter image or shape for fish bone is clearly shown in contrast to darker images for soft tissues.

However, the abnormal object carelessly swallowed or eaten is often considerable small like fish bone with an appearance similar to a tiny long pin, and the posture of the abnormal object always influences the brightness and size of the X-ray image. For example, an erect abnormal object has a brighter and larger X-ray image, and is easy to recognize, but an oblique abnormal object is often carelessly neglected or misjudged by the doctor because of darker and vaguer X-ray image. Further, the abnormal object is easily affected by other surrounding tissues, as a result of visionary interference.

In particular, the older or the patient suffering from chronical disease has poor perception, and does not obviously feel painful or uncomfortable when the abnormal object is stuck in the throat at a specific location or with a special posture. Then, the abnormal object is neglected or the doctor is distracted in diagnosis, and the abnormal object will stay in the throat for a long time. Because the abnormal object is constantly pushed by water or food swallowed or eaten, the gullet or surrounding blood vessels like neck artery might be penetrated and seriously damaged, leading to abrupt bleeding and even a fatal situation. It is crucial to correctly and fast recognize the abnormal object stuck in the throat part.

Overall, experienced doctors are able to correctly determine the abnormal object stuck in the throat part by inspecting a plurality of X-ray images at different exposure angles. However, vision fatigue often happens to the doctors, and the accumulated X-ray exposure for the patient possibly causes adverse effects on health. Thus, inspection of the abnormal object by human vision is not an effective option. Clinically, it often fails to confirm at the first time that fish bone is stuck in the throat part from the X-ray image, and the patient needs to be further treated by other medical inspections like computerized axial tomography (CAT) scan (or CT for short). However, CT will increase radiation onto the patient. Also, medication cost is increased because the patient has to stay more days in the hospital for further inspection. It is thus helpful to fast and correctly judge the X-ray image for reducing medication cost and preventing any precious medical resource from wasting.

Therefore, it is greatly needed to provide a new system and method of throat abnormal object recognition, wherein the system comprises a throat abnormal object recognition device, a data source device, a display device, and an operation device connected to the throat abnormal object recognition device, the data source device, and the display device, and particularly, the method comprises: employing the throat abnormal object recognition device to generate operation parameters; employing the data source device to generate an original X-ray image data; the throat abnormal object recognition device reading the original X-ray image data; performing a pre-stage process on the original X-ray image data to generate a pre-stage processed image data; performing a comparison process on the pre-stage processed image data to generate a comparison processed image data with an abnormal object image; employing a frame mark to mark the abnormal object image as a mark X-ray image; and employing the display device to display the mark X-ray image, thereby overcoming the above problems in the prior arts.

SUMMARY OF THE INVENTION

The primary object of the present invention is to provide a system of throat abnormal object recognition comprising a throat abnormal object recognition device, an operation device, a data source device, and a display device for recognizing any throat abnormal object, and the throat abnormal object recognition device, the data source device, and the display device are connected to the operation device. The throat abnormal object recognition device provides a learning recognition mode and an auxiliary recognition mode, and the auxiliary recognition mode is intended to implement a function of throat abnormal object recognition. The operation device is provided for a user to operate and communicate with the throat abnormal object recognition device, and switches the throat abnormal object recognition device into the learning recognition mode or the auxiliary recognition mode. The data source device stores at least one of reference X-ray image data and at least one of original X-ray image data for the operation device to read. Specifically, each of the at least one of reference X-ray image data comprises a red image data, a green image data, and a blue image data, and accordingly, each of the at least one of original X-ray image data comprises a red image data, a green image data, and a blue image data. In addition, the display device is provided with a display function.

Further, the throat abnormal object recognition device comprises a throat abnormal object recognition unit and an operation parameter memory, and the throat abnormal object recognition unit is connected to the operation parameter memory and the operation device.

When the throat abnormal object recognition device enters the learning recognition mode, the throat abnormal object recognition unit reads the at least one of reference X-ray image data from the data source device through the operation device, and performs a learning recognition process to generate and transmit a plurality of operation parameters to the data source device for storing.

Each the at least one of reference X-ray image data comprises a reference mark data, and the reference mark data comprises a throat image responsive of a side view of a throat part referring to a region ranging from a mouth to a gullet in a neck. Specifically, the reference mark data further comprises a frame mark, a point mark, or a coordinates mark for marking a reference abnormal object in the throat part. Further, the frame mark is intended to enclose the reference abnormal object, the point mark indicates a central point of the reference abnormal object, and the coordinates mark comprises coordinates of the central point of the reference abnormal object, or coordinates of two opposite corners of a rectangle for accommodating the reference abnormal object.

Additionally, when the throat abnormal object recognition device enters the auxiliary recognition mode, the throat abnormal object recognition processing unit reads the plurality of operation parameters from the data source device, then reads the at least one of original X-ray image data from the data source device through the operation device, performs a throat abnormal object recognition process based on the plurality of operation parameters to recognize or identify a throat abnormal object in the throat part, and generates a mark X-ray image data. The mark X-ray image data is then transmitted to the operation device.

Next, the operation device transmits the mark X-ray image data to the display device to display a mark X-ray image responsive to the mark X-ray image data, and the mark X-ray image comprises the frame mark to mark the throat abnormal object.

Further, another object of the present invention is to provide a method of throat abnormal object recognition. First, the method employs a throat abnormal object recognition device to connect an operation device, and the operation device is further connected to a data source device. Then, the operation device is employed to switch the throat abnormal object recognition device to enter a learning recognition mode or an auxiliary recognition mode.

If the throat abnormal object recognition device enters the learning recognition mode, the data source device transmits a reference X-ray image data and a mark data to the operation device. The reference X-ray image data comprises a throat image responsive of a side view of a throat part referring to a region ranging from a mouth to a gullet in a neck, the mark data comprises a frame mark, a point mark, or a coordinates mark for marking a reference abnormal object in the throat part. Specifically, the frame mark is intended to enclose the reference abnormal object, the point mark indicates a central point of the reference abnormal object, the coordinates mark comprises coordinates of the central point of the reference abnormal object or coordinates of two opposite corners of a rectangle for accommodating the reference abnormal object.

Next, the throat abnormal object recognition processing unit reads the reference X-ray image data and the mark data through the operation device, and the throat abnormal object recognition processing unit performs a learning recognition pre-stage process on the reference X-ray image data to generate a learning recognition pre-stage processed image data.

Further, an abnormal object shape of the throat abnormal object in the frame mark is recognized or identified. Finally, the mark data and the abnormal object shape as operation parameters are generated and stored to the data source device, and the operation device then switches the throat abnormal object recognition device to enter the learning recognition mode or the auxiliary recognition mode for performing the subsequent steps.

If the throat abnormal object recognition device enters the auxiliary recognition mode, the data source device generates an original X-ray image data, and the original X-ray image data comprises a throat image data responsive to a side view of a throat part of a patient. Specifically, the original X-ray image data has a red image data, a green image data, and a blue image data.

Next, the throat abnormal object recognition device reads the original X-ray image data from the data source device through the operation device, and the throat abnormal object recognition device further performs an auxiliary recognition pre-stage process on the original X-ray image data to generate an auxiliary recognition pre-stage processed image data.

The throat abnormal object recognition device employs the operation parameters as a comparison rule to perform a comparison process on the auxiliary recognition pre-stage processed image data so as to generate a comparison processed image data. Further, the comparison process employs the operation parameters to search an abnormal object image in the auxiliary recognition pre-stage processed image data, and then generates an outline of the abnormal object as an abnormal object shape of the abnormal object.

Then, the throat abnormal object recognition device employs the frame mark to mark the abnormal object image, generates and transmits a mark X-ray image data to the operation device. For example, the mark X-ray image data comprises the mark data and the abnormal object shape responsive to the abnormal object. Finally, a display device connected to the operation device is employed to receive the mark X-ray image data from the throat abnormal object recognition device, and displays a mark X-ray image responsive to the mark X-ray image data, and the operation device then switches the throat abnormal object recognition device to enter the learning recognition mode or the auxiliary recognition mode.

Overall, the present invention employs the throat abnormal object recognition device to recognize the abnormal object stuck in the throat part from the original X-ray image data, and clearly indicates the location of the abnormal object by the frame mark so as to help doctors fast and precisely diagnose the patient and identify the abnormal object for effective treatment without delay, In particular, the operation parameters stored in the operation parameter memory for recognizing various types of the abnormal objects including shapes and postures are used to build a database for reference and comparison in the subsequent auxiliary recognition process, thereby greatly improving correctness and preciseness of abnormal object recognition. Furthermore, the operation parameters are generated through learning according to the reference samples with the typical marked abnormal objects.

BRIEF DESCRIPTION OF THE DRAWINGS

The present invention can be understood in more detail by reading the subsequent detailed description in conjunction with the examples and references made to the accompanying drawings, wherein.

DETAILED DESCRIPTION OF THE PREFERRED EMBODIMENT

The present invention may be embodied in various forms and the details of the preferred embodiments of the present invention will be described in the subsequent content with reference to the accompanying drawings. The drawings (not to scale) show and depict only the preferred embodiments of the invention and shall not be considered as limitations to the scope of the present invention. Modifications of the shape of the present invention shall too be considered to be within the spirit of the present invention.

Figure 1:
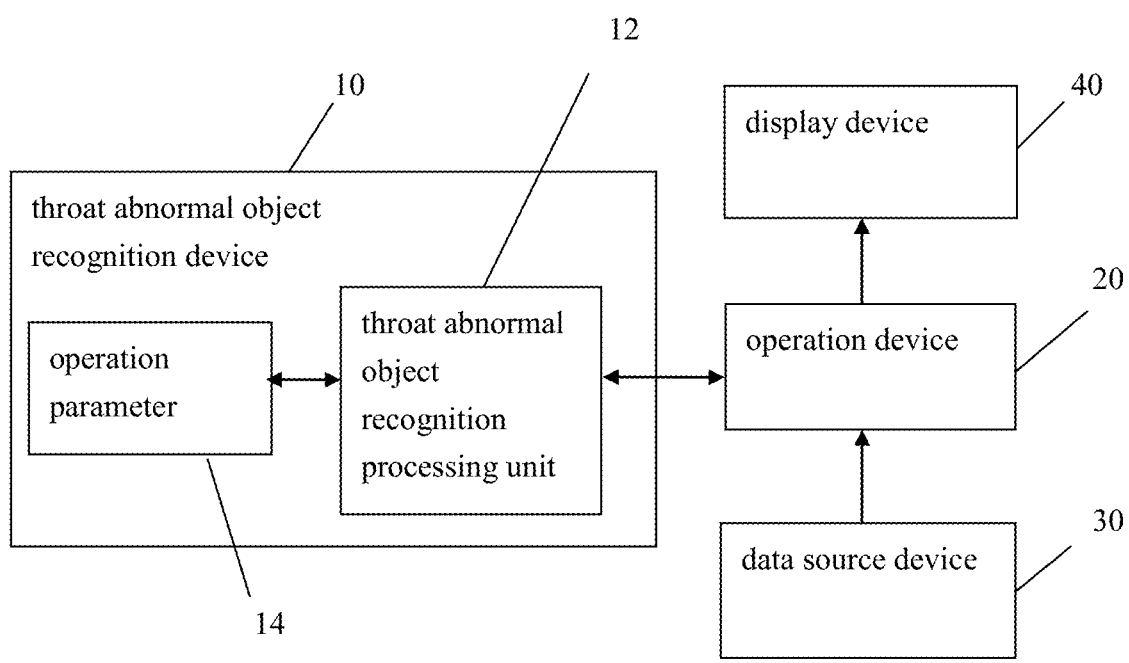
FIG. 1 is a view showing the system of throat abnormal object recognition according to the first embodiment of the present invention.

Please refer to FIG. 1 illustrating the system of throat abnormal object recognition according to the first embodiment of the present invention. As shown in FIG. 1, the system of throat abnormal object recognition of the first embodiment generally comprises a throat abnormal object recognition device 10, an operation device 20, a data source device 30, and a display device 40 for recognizing a throat abnormal object and assisting a doctor to fast diagnose the abnormal object and the location in the throat part to take necessary measures without delay.

Specifically, the throat abnormal object recognition device 10 provides a learning recognition mode and an auxiliary recognition mode as an operation mode, and the auxiliary recognition mode implements a function of throat abnormal object recognition. It is preferred that the throat abnormal object recognition device 10 is implemented by a micro-computer, a micro controller (MCU), or a microprocessor executing an operation system like Linux OS as well as applications like Tensor Flow developed by google company. The operation device 20 comprises an electronic device selected from a group consisting of a personal computer, a laptop computer, a tablet computer, a smart phone, and a terminal, and the data source device 30 comprises an X-ray machine for generating an X-ray image data comprising an X-ray image.

Further, the operation device 20 is connected to the throat abnormal object recognition device 10 for communication and intended for the user like doctor or medical personnel to operate and switch the throat abnormal object recognition device 10 to enter the auxiliary recognition mode, or the auxiliary recognition mode. The data source device 30 is connected to the operation device 20, and stores at least one of reference X-ray image data and at least one of original X-ray image data for the operation device 20 to read. Each of the at least one of reference X-ray image data comprises a red image data, a green image data, and a blue image data, and accordingly, each of the at least one of original X-ray image data comprises a red image data, a green image data, and a blue image data. Specifically, the reference X-ray image data and the original X-ray image data primary include a side view of the throat region, and are commonly used for the X-ray machine in the prior arts. Thus, the aspects of the reference X-ray image data and the original X-ray image data will not be described in detail hereinafter.

Additionally, the display device 40 like liquid crystal display (LCD) is provided with an image display function, and connected to the operation device 20.

Further, the throat abnormal object recognition device 10 comprises a throat abnormal object recognition processing unit 12 and an operation parameter memory 14, and the throat abnormal object recognition processing unit 12 is connected to the operation parameter memory 14 and the operation device 20. The operation parameter memory 14 stores a plurality of operation parameters previously generated for the throat abnormal object recognition processing unit 12 to recognize the abnormal object in the throat part or region. In particular, the throat part refers to the region ranging from a mouth to a gullet in a neck.

More specifically, when the throat abnormal object recognition device 10 enters the learning recognition mode as the operation mode, the throat abnormal object recognition processing unit 12 reads the at least one of reference X-ray image data from the data source device 30 through the operation device 20, and performs a learning recognition process on the at least one of reference X-ray image data to generate and transmit the operation parameters to the data source device 14 for storing.

Each of the at least one of reference X-ray image data comprises a reference mark data, and the reference mark data comprises a throat image responsive of the side view of the throat part. For instance, the reference mark data further comprises a frame mark, a point mark, or a coordinates mark for marking a reference abnormal object in the throat part. Specifically, the frame mark is intended to enclose the reference abnormal object, the point mark indicates a central point of the reference abnormal object, and the coordinates mark comprises coordinates of the central point of the reference abnormal object or coordinates of two opposite corners of a rectangle for accommodating the reference abnormal object.

For example, the frame mark comprises a rectangular frame, an oval frame, or a curved and closed frame.

In addition, when the throat abnormal object recognition device 10 enters the auxiliary recognition mode as the operation mode, the throat abnormal object recognition processing unit 12 reads the operation parameters from the data source device 14, reads the at least one of original X-ray image data from the data source device 30 through the operation device 20, performs a throat abnormal object recognition process based on the operation parameters to recognize or identify a throat abnormal object in the throat part, and generate a mark X-ray image data. The mark X-ray image data is then transmitted to the display device 40 through the operation device 20 for displaying a mark X-ray image responsive to the mark X-ray image data. The mark X-ray image comprises the frame mark to mark the throat abnormal object. Also, the original X-ray image data can be transmitted to the display device 40 through the operation device 20 for displaying an original X-ray image responsive to the original X-ray image data. In short, the user or doctor are able to view the mark X-ray image and the original X-ray image at a time for comparison and examination, thereby confirming the related information for the abnormal object stuck in the throat part of the patient like location, shape, size, and posture of a fish bone.

The above learning recognition process comprises: performing a learning recognition pre-stage process on the reference X-ray image data to generate a learning recognition pre-stage processed image data: recognizing or identifying an abnormal object shape of the throat abnormal object in the frame mark; and generating and storing the reference mark data and the abnormal object shape as the operation parameters, then the operation device switching the throat abnormal object recognition device 10 to enter the learning recognition mode or the auxiliary recognition mode for the subsequent steps.

Furthermore, the above throat abnormal object recognition process comprises an auxiliary recognition pre-stage process, a comparison process, and a mark process.

The an auxiliary recognition pre-stage process comprises: selecting one of the red image data, the green image data, and the blue image data of the original X-ray image responsive to the original X-ray image data as a target image data, or calculating an arithmetic average image data of the red image data, the green image data, and the blue image data of the original X-ray image as the target image data, performing a gray leveling treatment on the target image data to generate a single color levelled image data; adjusting a contrast of the single color levelled image data image data to generate a contrast image data; and adjusting a sharpness of the contrast image data to generate a sharp image data as a pre-stage processed image data. It is preferred that the contrast is adjusted within 0.9 and 1.1, and the sharpness is adjusted within 200% and 300%.

Further, the comparison process is performed by employing the operation parameters as a comparison rule to search an abnormal object image in the pre-stage processed image data, and mark process is performed by marking the abnormal object image by the frame mark to generate the mark X-ray image data as desired.

Figure 2:
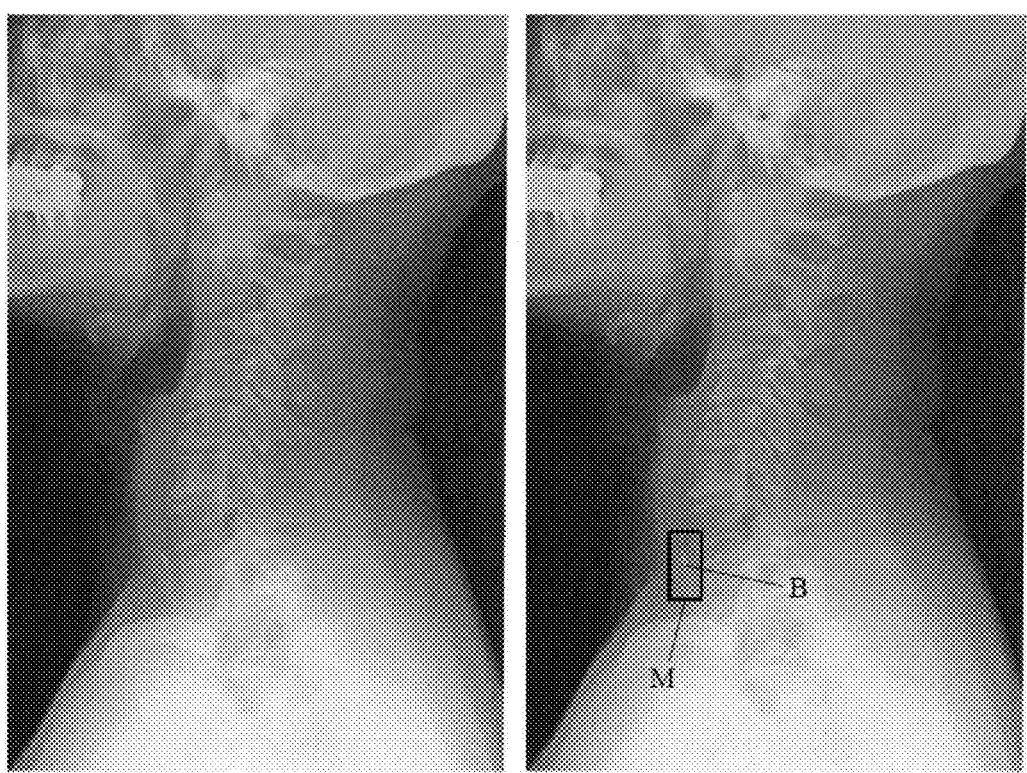
FIG. 2 is a view showing the mark X-ray image and the original X-ray image used in the system according to the first embodiment of the present invention.

Refer to FIG. 2 illustrating the mark X-ray image and the original X-ray image used in the system according to the first embodiment of the present invention. As shown in FIG. 2, the mark X-ray image is at the right side and the original X-ray image is at the left side. The mark X-ray image data comprises the frame mark M for marking the throat abnormal object B. In particular, the throat abnormal object B is within the frame mark M. For example, the frame mark M comprises a rectangular frame, an oval frame, or a curved and closed frame, and FIG. 2 only shows the rectangular frame as an example for clear explanation, and is not intended to limit the scope of the present invention.

Figure 3:
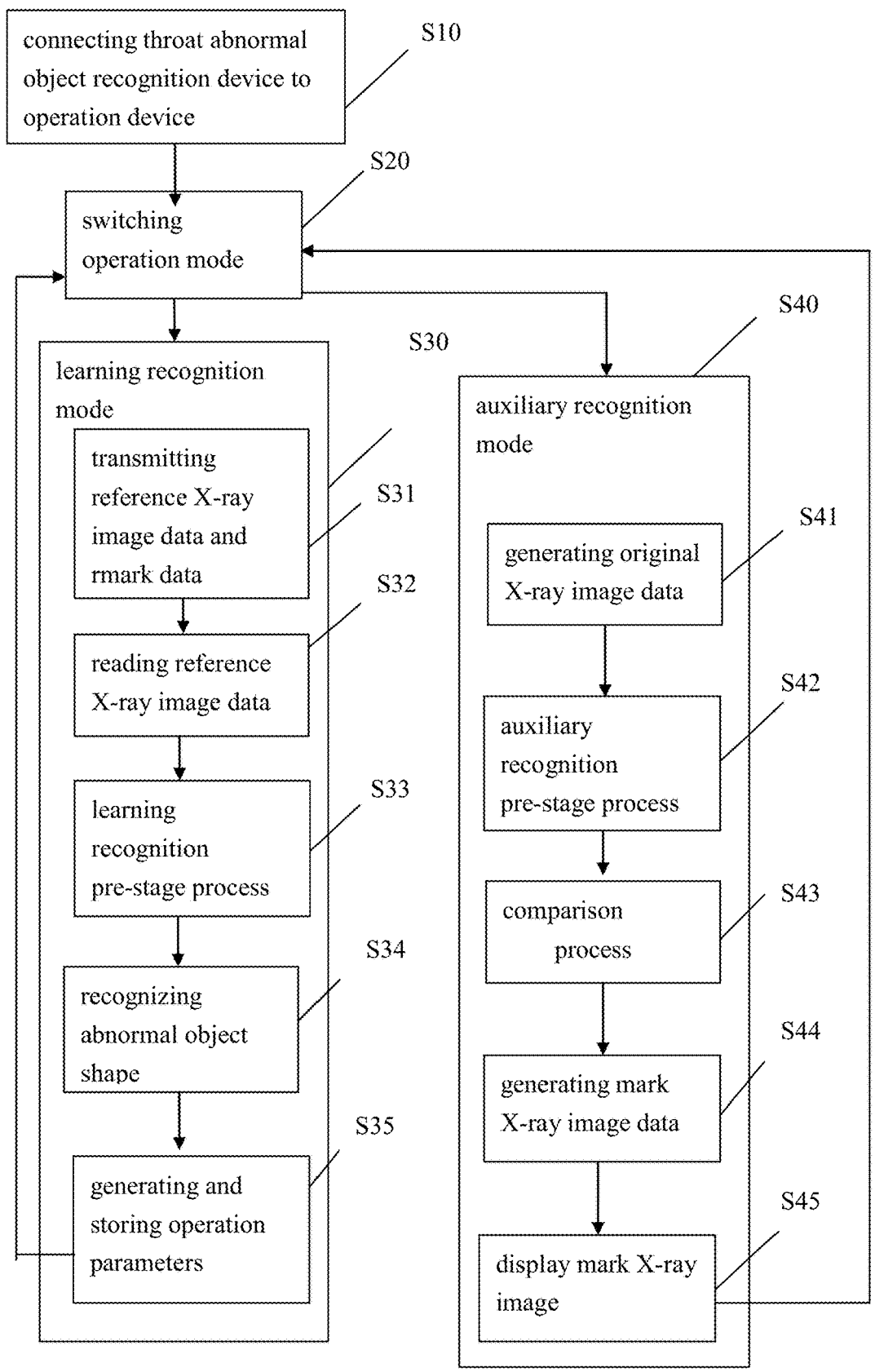
FIG. 3 is a flowchart showing the method of throat abnormal object recognition according to the second embodiment of the present invention.

Then, refer to FIG. 3 illustrating the flowchart showing the method of throat abnormal object recognition according to the second embodiment of the present invention. As shown in FIG. 3, the method of throat abnormal object recognition comprises the steps S10, S20, S30, and S40 for implementing a function of throat abnormal recognition.

Specifically, the step S10 is performed by employing a throat abnormal object recognition device to connect an operation device connected to a data source device, and in the step S20, the operation device is employed to switch the throat abnormal object recognition device to enter a learning recognition mode or an auxiliary recognition mode as an operation mode.

If the throat abnormal object recognition device is in the learning recognition mode as the operation mode, the step S30 is performed and comprises the sequential steps S31, S32, S33, S34, and S35, and if the throat abnormal object recognition device is in the auxiliary recognition mode as the operation mode, the step S40 is performed and comprises the sequential steps S41, S42, S43, S44, and S45.

Specifically, for the step S31 in the learning recognition mode, the data source device transmits a reference X-ray image data and a mark data to the operation device. The reference X-ray image data comprises a throat image responsive of a side view of a throat part referring to a region ranging from a mouth to a gullet in a neck, and the mark data comprises a frame mark, a point mark, or a coordinates mark for marking a reference abnormal object in the throat part. The frame mark is intended to enclose the reference abnormal object, the point mark indicates a central point of the reference abnormal object, and the coordinates mark comprises coordinates of the central point of the reference abnormal object or coordinates of two opposite corners of a rectangle for accommodating the reference abnormal object.

In the step S32, the throat abnormal object recognition processing unit reads the reference X-ray image data and the mark data through the operation device, and in the step S33, the throat abnormal object recognition processing unit performs a learning recognition pre-stage process on the reference X-ray image data to generate a learning recognition pre-stage processed image data.

Then, the step S34 is performed by recognizing or identifying an abnormal object shape of the throat abnormal object in the frame mark. Finally, the step S35 is performed, the mark data and the abnormal object shape as operation parameters are generated and stored to the data source device, the step S20 is then performed, and the operation device switches the throat abnormal object recognition device to enter the learning recognition mode or the auxiliary recognition mode to perform the subsequent operations.

In other words, the primary effect of the learning recognition mode is to build a database comprising the operation parameters based on the reference X-ray image data and the mark data to implement the purpose of learning.

In addition, for the step S41 in the auxiliary recognition mode, the data source device generates an original X-ray image data. The original X-ray image data comprises a throat image data responsive to a side view of a throat part of a patient, and the original X-ray image data has a red image data, a green image data, and a blue image data.

In the step S42, the throat abnormal object recognition device reads and performs an auxiliary recognition pre-stage process on the original X-ray image data from the data source device through the operation device to generate an auxiliary recognition pre-stage processed image data, and in the step S43, the throat abnormal object recognition device employs the operation parameters from the operation parameter memory as a comparison rule to perform a comparison process on the auxiliary recognition pre-stage processed image data to generate a comparison processed image data. The comparison process employs the operation parameters to search an abnormal object image in the auxiliary recognition pre-stage processed image data, and generates an outline of the abnormal object as an abnormal object shape of the abnormal object.

Next, the step S44 is performed and the throat abnormal object recognition device employs the frame mark to mark the abnormal object image, then generates and transmits a mark X-ray image data to the operation device. The mark X-ray image data comprises the mark data and the abnormal object shape responsive to the abnormal object.

In the step S45, a display device connected to the operation device is employed to receive the mark X-ray image data from the throat abnormal object recognition device, and display a mark X-ray image responsive to the mark X-ray image data, and then the operation device switches the throat abnormal object recognition device to enter the learning recognition mode or the auxiliary recognition mode to perform the subsequent operations.

In short, the key effect of the auxiliary recognition mode is to search the abnormal object in the throat part based on the original X-ray image data and the operation parameters to assist the doctor for correct diagnosis. It does not only save the manpower cost, but also avoids vision weariness, speeds up diagnosis, and greatly increases accuracy of diagnosis for the abnormal object in the throat part.

From the above mention, the aspect of the present invention is that the throat abnormal object recognition processing unit of the throat abnormal object recognition device performs the process of abnormal object recognition on the side view of the X-ray image to search the abnormal object in the throat part, and further uses the frame mark to mark the abnormal object to assist the doctor to fast diagnose and confirm the location of the abnormal object for further medical treatment without delay.

Another aspect of the present invention is that the learning recognition mode to build the database comprising the operation parameters for the subsequent auxiliary recognition mode to reference. In particular, the operation parameters cover various shapes and postures of the abnormal object so as to increase accuracy of diagnosis. Specifically, accuracy of diagnosis is increased from 84% in the prior arts up to 94%, thereby truly helping the doctor for fast and correct diagnosis.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A system of throat abnormal object recognition, comprising:
a throat abnormal object recognition device providing a learning recognition mode and an auxiliary recognition mode, the auxiliary recognition mode implementing a function of throat abnormal object recognition;
an operation device connected to and communicating with the throat abnormal object recognition device for an user to operate and control the throat abnormal object recognition device to enter the learning recognition mode or the auxiliary recognition mode as an operation mode;
a data source device connected to the operation device for storing at least one of reference X-ray image data and at least one of original X-ray image data for the operation device to read, each of the at least one of reference X-ray image data comprising a red image data, a green image data, and a blue image data, each of the at least one of original X-ray image data comprising a red image data, a green image data, and a blue image data; and
a display device connected to the operation device for implementing an image display function,
wherein the throat abnormal object recognition device comprises a throat abnormal object recognition processing unit and an operation parameter memory, the throat abnormal object recognition processing unit is connected to the operation parameter memory and the operation device,
wherein when the throat abnormal object recognition device enters the learning recognition mode, the throat abnormal object recognition processing unit reads the at least one of reference X-ray image data from the data source device through the operation device, and performs a learning recognition process to generate and transmit a plurality of operation parameters to the data source device for storing, each the at least one of reference X-ray image data comprises a reference mark data, the reference mark data comprises a throat image responsive of a side view of a throat part referring to a region ranging from a mouth to a gullet in a neck, the reference mark data further comprises a frame mark, a point mark, or a coordinates mark for marking a reference abnormal object in the throat part, the frame mark is intended to enclose the reference abnormal object, the point mark indicates a central point of the reference abnormal object, the coordinates mark comprises coordinates of the central point of the reference abnormal object or coordinates of two opposite corners of a rectangle for accommodating the reference abnormal object,
wherein when the throat abnormal object recognition device enters the auxiliary recognition mode, the throat abnormal object recognition processing unit reads the plurality of operation parameters from the data source device, reads the at least one of original X-ray image data from the data source device through the operation device, performs a throat abnormal object recognition process based on the plurality of operation parameters to recognize or identify a throat abnormal object in the throat part, and generate a mark X-ray image data, the mark X-ray image data is then transmitted to the operation device and the display device through the operation device, the display device displays a mark X-ray image responsive to the mark X-ray image data, the mark X-ray image comprises the frame mark to mark the throat abnormal object.

2. The system as claimed in claim 1, wherein the operation device comprises an electronic device selected from a group consisting of a personal computer, a laptop computer, a tablet computer, a smart phone, and a terminal, and the data source device comprises an X-ray machine.

3. The system as claimed in claim 1, wherein the frame mark comprises a rectangular frame, an oval frame, or a curved and closed frame, and the throat abnormal object is within the frame mark.

4. The system as claimed in claim 1, wherein the throat abnormal object recognition process comprises:
an auxiliary recognition pre-stage process comprising: selecting one of the red image data, the green image data, and the blue image data of the original X-ray image responsive to the original X-ray image data as a target image data, or calculating an arithmetic average image data of the red image data, the green image data, and the blue image data of the original X-ray image as the target image data, performing a gray leveling treatment on the target image data to generate a single color levelled image data; adjusting a contrast of the single color levelled image data image data to generate a contrast image data, the contrast being adjusted within 0.9 and 1.1; and adjusting a sharpness of the contrast image data to generate a sharp image data as a pre-stage processed image data, the sharpness being adjusted within 200% and 300%;
a comparison process employing the operation parameters as a comparison rule to search an abnormal object image in the pre-stage processed image data; and
a mark process marking the abnormal object image by the frame mark to generate the mark X-ray image data.

5. The system as claimed in claim 1, wherein the learning recognition process comprises:
performing a learning recognition pre-stage process on the reference X-ray image data to generate a learning recognition pre-stage processed image data;
recognizing or identifying an abnormal object shape of the throat abnormal object in the frame mark; and
generating and storing the reference mark data and the abnormal object shape as the operation parameters, then the operation device switching the throat abnormal object recognition device to enter the learning recognition mode or the auxiliary recognition mode.

6. A method of throat abnormal object recognition, comprising:
employing a throat abnormal object recognition device to connect an operation device connected to a data source device,
employing the operation device to switch the throat abnormal object recognition device to a learning recognition mode or an auxiliary recognition mode as an operation mode;
in case of the throat abnormal object recognition device in the learning recognition mode, performing steps of:
the data source device transmitting a reference X-ray image data and a mark data to the operation device, the reference X-ray image data comprising a throat image responsive of a side view of a throat part referring to a region ranging from a mouth to a gullet in a neck, the mark data comprising a frame mark, a point mark, or a coordinates mark for marking a reference abnormal object in the throat part, the frame mark intended to enclose the reference abnormal object, the point mark indicating a central point of the reference abnormal object, the coordinates mark comprising coordinates of the central point of the reference abnormal object or coordinates of two opposite corners of a rectangle for accommodating the reference abnormal object;
the throat abnormal object recognition processing unit reading the reference X-ray image data and the mark data through the operation device;
the throat abnormal object recognition processing unit performing a learning recognition pre-stage process on the reference X-ray image data to generate a learning recognition pre-stage processed image data;
recognizing or identifying an abnormal object shape of the throat abnormal object in the frame mark; and
generating and storing the mark data and the abnormal object shape as operation parameters to the data source device, then the operation device switching the throat abnormal object recognition device to enter the learning recognition mode or the auxiliary recognition mode,
in case of the throat abnormal object recognition device in the auxiliary recognition mode, performing steps of:
the data source device generating an original X-ray image data, the original X-ray image data comprising a throat image data responsive to a side view of a throat part of a patient, the original X-ray image data having a red image data, a green image data, and a blue image data,
the throat abnormal object recognition device reading the original X-ray image data from the data source device through the operation device;
the throat abnormal object recognition device performing an auxiliary recognition pre-stage process on the original X-ray image data to generate an auxiliary recognition pre-stage processed image data;
the throat abnormal object recognition device employing the operation parameters from the operation parameter memory as a comparison rule to perform a comparison process on the auxiliary recognition pre-stage processed image data to generate a comparison processed image data, the comparison process employing the operation parameters to search an abnormal object image in the auxiliary recognition pre-stage processed image data, and generating an outline of the abnormal object as an abnormal object shape of the abnormal object;
the throat abnormal object recognition device employing the frame mark to mark the abnormal object image, generating and transmitting a mark X-ray image data to the operation device, the mark X-ray image data comprising the mark data and the abnormal object shape responsive to the abnormal object; and
employing a display device connected to the operation device to receive the mark X-ray image data from the throat abnormal object recognition device, and display a mark X-ray image responsive to the mark X-ray image data, and then the operation device switching the throat abnormal object recognition device to enter the learning recognition mode or the auxiliary recognition mode.

7. The method as claimed in claim 6, wherein the operation device comprises an electronic device selected from a group consisting of a personal computer, a laptop computer, a tablet computer, a smart phone, and a terminal, and the data source device comprises an X-ray machine.

8. The method as claimed in claim 6, wherein the frame mark comprises a rectangular frame, an oval frame, or a curved and closed frame, and the throat abnormal object is within the frame mark.

9. The method as claimed in claim 6, wherein the auxiliary recognition pre-stage process comprises:
performing a gray leveling treatment on the original image data to generate a single color levelled image data;
adjusting a contrast of the single color levelled image data image data to generate a contrast image data; and adjusting a sharpness of the contrast image data to generate a sharp image data as a pre-stage processed image data.

10. The method as claimed in claim 9, wherein the gray leveling treatment is performed on a target image data, the target image data is selected from one of the red image data, the green image data, and the blue image data of an original X-ray image responsive to the original X-ray image data, or the target image data is an arithmetic average image data of the red image data, the green image data, and the blue image data of the original X-ray image, the contrast is adjusted within 0.9 and 1.1, and the sharpness is adjusted within 200% and 300%.

* * * * *